United States Patent [19]

Moo-Young et al.

[11] Patent Number: 5,756,115
[45] Date of Patent: May 26, 1998

[54] CONTRACEPTIVE METHOD USING A SUBDERMALLY IMPLANTABLE DEVICE

[75] Inventors: Alfred Joseph Moo-Young. Hastings-On-Hudson, N.Y.; Horacio Bruno Croxatto, Santiago, Chile

[73] Assignee: The Population Coucil, Center for Biomedical Research, New York, N.Y.

[21] Appl. No.: 478,418

[22] Filed: Jun. 7, 1995

Related U.S. Application Data

[62] Division of Ser. No. 333,279, Oct. 2, 1994, Pat. No. 5,660, 848.

[51] Int. Cl.$^6$ .............. A61F 6/06; A61F 6/14; A61F 47/38
[52] U.S. Cl. .............. 424/425; 424/430; 424/433; 514/843
[58] Field of Search .............. 424/422, 425, 424/430, 433, DIG. 12, DIG. 13; 514/843

[56] References Cited

U.S. PATENT DOCUMENTS

| | | | |
|---|---|---|---|
| 3,625,214 | 12/1971 | Higuchi | 424/424 |
| 3,832,252 | 8/1974 | Higuchi et al. | 156/86 |
| 3,854,480 | 12/1974 | Zaffaroni | 424/424 |
| 3,926,188 | 12/1975 | Baker et al. | 128/260 |
| 3,948,254 | 4/1976 | Zaffaroni | 424/423 |
| 3,992,518 | 11/1976 | Chien et al. | 424/425 |
| 3,993,072 | 11/1976 | Zaffaroni | 424/430 |
| 4,053,580 | 10/1977 | Chien et al. | 424/15 |
| 4,244,949 | 1/1981 | Gupta | 424/243 |
| 4,351,337 | 9/1982 | Sidman | 128/260 |

(List continued on next page.)

FOREIGN PATENT DOCUMENTS

| | | |
|---|---|---|
| 1412970 | 11/1975 | United Kingdom . |
| 2010676 | 7/1979 | United Kingdom . |
| 2136688 | 9/1984 | United Kingdom . |
| 2154138 | 9/1985 | United Kingdom . |
| 9321859 | 11/1993 | WIPO . |
| 9406437 | 3/1994 | WIPO . |

OTHER PUBLICATIONS

Haukkamaa et al., Contraception 45(1):49–55 (1992).
Laurikka—Routti, Obstet. Gynecol. 80(5):855–59 (1992).
Coutinho et al., Int. J. Fertil. Steril. 21:103–08 (1976).
Lahteenmaki et al., Contraception 25:299–306 (1982).
Sujan et al., Contraception 50:27–34 (1994).
Coutinho et al., Int. J. Fertil. Steril. 36:737–40 (1981).
Diaz et al., Contraception 44(4):393–408 (1991).
Laurikka-Routti et al., Fert. Steril. 58(6):1142–47 (1992).
Robertson et al., Contraception, 31(4):351–359 (1985).
Odlind, et al., Long–Acting Contraceptive Delivery Systems, pp. 441–449 (1984).
Suhonen, et al., Fert. Steril. 57(6):1211–1215 (1992).

*Primary Examiner*—Edward J. Webman
*Attorney, Agent, or Firm*—Lerner, David, Littenberg, Krumholz & Mentlik

[57] ABSTRACT

Disclosed is a subdermally implantable drug-delivery device, which contains: a central core extending in an axial direction and having an outer surface and opposing ends, which core includes a matrix of a pharmaceutically effective amount of a subdermally administrable drug substantially uniformly dispersed in a polymeric base material; an intermediate polymeric layer overlying the outer surface of the central core; and an outer polymeric layer overlying the intermediate layer, wherein the intermediate layer controls the rate of diffusion of the drug from the central core to the outer layer. In preferred embodiments, the subdermally administrable drug is a contraceptive agent such as the 16-methylene-17-α-acetoxy-19-norprogesterone-progestin; the polymeric base material and the outer polymeric layer each contain a polydimethylsiloxane such as Silastic®; and the intermediate layer contains a porous material such as cellulose. The devices provide for the substantially zero-order release of the drug for their intended lifetime without initial overdosing of the drug.

29 Claims, 2 Drawing Sheets

U.S. PATENT DOCUMENTS

| | | | |
|---|---|---|---|
| 4,609,374 | 9/1986 | Ayer | 424/473 |
| 4,639,244 | 1/1987 | Rizk et al. | 604/19 |
| 4,666,704 | 5/1987 | Shalati et al. | 424/424 |
| 4,920,727 | 5/1990 | Ristimaki et al. | 53/252 |
| 4,952,403 | 8/1990 | Vallee et al. | 424/422 |
| 4,957,119 | 9/1990 | De Nijs | 604/890.1 |
| 5,035,891 | 7/1991 | Runkel et al. | 424/423 |
| 5,057,317 | 10/1991 | Iida | 424/423 |
| 5,141,748 | 8/1992 | Rizzo | 424/425 |
| 5,150,718 | 9/1992 | De Nijs | 604/890.1 |

CONTRACEPTIVE METHOD USING A SUBDERMALLY IMPLANTABLE DEVICE

This is a division of application Ser. No. 08/333,279 filed Oct. 2, 1994, now U.S. Pat. No. 5,660,848.

Financial support for the invention described herein was received from the U.S. Agency for International Development under Cooperative Agreement No. DPE-3050-A-00-8059-00. Therefore, the U.S. Government may have certain rights in the invention.

FIELD OF THE INVENTION

The disclosed invention relates to subdermally implantable devices which provide for the sustained release of a pharmaceutically effective amount of a drug to a subject.

BACKGROUND OF THE INVENTION

In many therapeutic programs pertaining to the management of health and disease, the use of drug delivery devices which provide for the slow release of a drug to the body at a controlled rate over a prolonged period of time to achieve a desired physiologic or pharmacologic effect has proved beneficial. A principal advantage of employing sustained-release compositions is that many therapeutic agents would otherwise be rapidly metabolized or cleared from the patient's system necessitating frequent administration of the drug to maintain a therapeutically effective concentration.

Accordingly, a variety of sustained release devices have been designed for oral, rectal and subcutaneous administration. "Matrix" type devices typically consist of an active compound dispersed in a matrix of carrier material which may be either porous or non-porous, solid or semi-solid, and permeable or impermeable to the active compound. These devices are rather easily prepared; however, they are not suitable for administering some pharmacologically active compounds. In addition, the rate of release of the active compound decreases with time. "Reservoir" type devices consist of a central reservoir of active compound surrounded by a rate controlling membrane (rcm). The rcm is generally a porous or a non-porous material which is non-biodegradable. In the case of the transdermal devices of this type, to maintain an effective concentration of active compound, the rate controlling membrane must have a large surface area. Thus, a common disadvantage of these devices is that their large size makes administration quite inconvenient. Other sustained release devices are hybrid-type devices which contain a matrix core surrounded by a rcm. Yet other devices are mechanical in nature, and include active compound-filled electrical or osmotic pumps. These devices require frequent replacement. In addition, they have proved to be too large and expensive to be practical.

There has been a consistently large demand for the development of new, long-acting contraceptives that require minimal medical guidance. This is particularly the case in less developed countries where medical and family planning organizations are inadequate. Accordingly, several contraceptive implant systems (used hereinafter interchangeably with "devices") have been developed. For example, the Norplant® system contains six 3.4 cm capsules, each containing crystals of the synthetic progestin, levonorgestrel. When implanted subdermally, levonorgestrel diffuses through the polydimethylsiloxane (Silastic®) capsules. The contraceptive agent, 16-methylene-17α-acetoxy-19-nor-4-pregnene-3, pregene-3, 20 dione, or 16-methylene-17-α-acetoxynorprogesterone-(Nestorone™), has also been used in similar devices. See Coutinho et al., Int. J. Fertil. Steril. 21: 103–08 (1976). However, such contraceptive capsules have been criticized as being too short-lived and thus unsuitable for long-term contraception. See, e.g., Coutinho et al., Fertil. Steril. 36: 737–40 (1981) (disclosing that the implants had to be changed after six months); and Lahteenmäki et al., Contraception 25: 299–306 (1982) and Odlind et al., "Development of an Implant," in Zatuchni et al. (eds), Long-Acting Contraceptive Delivery Systems, Philadelphia, Harper and Row, pp. 441–49 (1984) (both reporting that the silastic implants were exhausted in less than one year). Subsequently, the Norplant II contraceptive system was developed. The Norplant II system contains two 4 cm implants, which together deliver a contraceptive effective dose of levonorgestrel for at least three years. Each implant consists of a rod-shaped drug matrix encased in a Silastic® tube sealed at both ends with an adhesive. Sujan et al., Contraception 50: 27–34 (1994). Although the Silastic® provides excellent biological compatibility with bodily fluids and tissues, they have also been found to allow for a rather high permeability to certain steroids.

It has been reported that the levonorgestrel present in the Norplant II system displays androgenic and hormonal side effects. See, e.g., Haukkamaa et al., Contraception 45(1): 49–55 (1992). Such side effects may be mitigated by the selection of other progestins such as the Nestorone™ progestin. However, the fact that this progestin is inactive when administered orally underscores the need to provide subdermally implantable contraceptive devices which are free of the disadvantages associated with prior art devices.

Although the ideal contraceptive implant may elude precise definition, there is general agreement in the field that the design of such an implant is complicated by several interrelated factors. First, the system must administer effective contraception for a period of at least about two years, and preferably about from 4 to 5 years, yet while at the same time minimizing the number of implants. The number of implants has been constrained by the amount of contraceptive agent needed, which in turn is dependent upon the potency of the chosen contraceptive agent. In addition, the device must release the contraceptive agent at a substantially constant rate (i.e., zero-order release) so as to avoid initial overdosing and depletion of the agent prior to the expiration of its intended useful lifetime. This factor is influenced by the solubility of the contraceptive agent in the various compartments of the device, the rate of diffusion of the active agent from the device, the surface area of the device, and the rate of removal of the active agent from bodily tissue surrounding the outer surface of the device. Further, the dimensions of the implant must be determined not only to take into account the release rate of the contraceptive, but also to impart the necessary rigidity to the device to facilitate its implantation. Even further, the device must be non-irritating and produce minimal side effects, as well as mechanically strong to withstand flexion or impact. Hence, a need remains for a subdermally implantable contraceptive device which fulfills at least some of these existing needs.

SUMMARY OF THE INVENTION

One embodiment of the present invention is directed to a subdermally implantable drug-delivery device, containing:

a central core extending in an axial direction and having an outer surface and opposing ends, the core including a matrix of a pharmaceutically effective amount of a subdermally administrable drug substantially uniformly dispersed in a polymeric base material;

an intermediate polymeric layer overlying the outer surface of the central core; and an outer polymeric layer overlying the intermediate layer, wherein the intermediate layer controls the rate of diffusion of the drug from the central core to the outer layer.

In a preferred embodiment, the axial ends of the central core and the intermediate layer are sealed. The subdermally administrable drug is preferably a contraceptive agent.

Another embodiment of the present invention is directed to a method of treating a mammalian or animal subject, which comprises the step of subdermally implanting the device in the subject, thus allowing for the sustained and controlled release of the drug to the subject for a predetermined time period. In a preferred embodiment, the present invention provides a method of contraception wherein the thus-implanted device administers a contraceptive effective amount of a contraceptive agent to the subject for a predetermined period of time.

DETAILED DESCRIPTION OF THE PREFERRED EMBODIMENTS

Figure 1A:
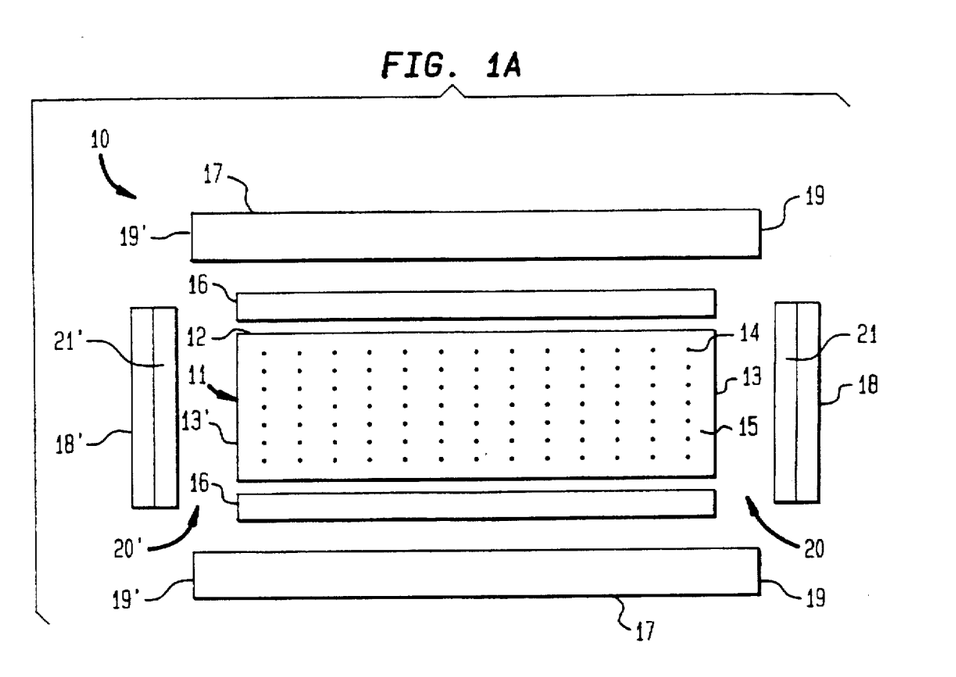
FIG. 1A is a longitudinal cross-sectional view of a partially assembled subdermally implantable device according to the present invention.
Figure 1B:
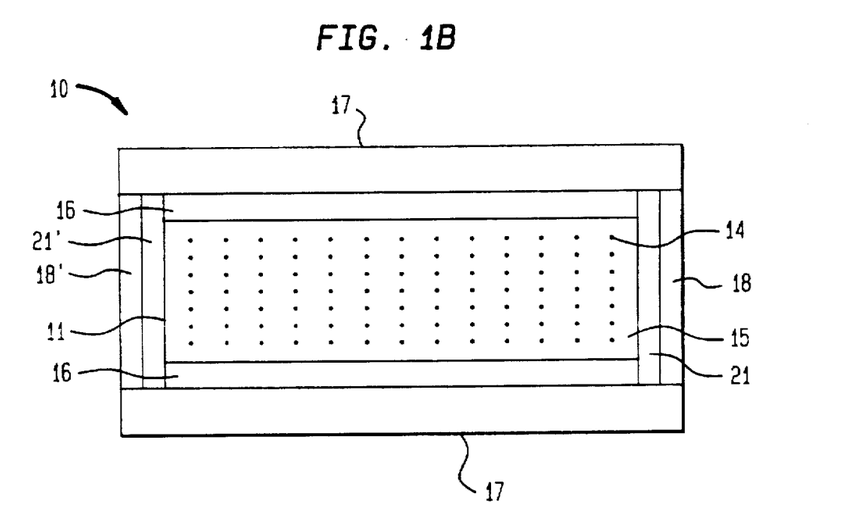
FIG. 1B is a longitudinal cross-sectional view of a completely assembled subdermally implantable device according to the present invention.

Turning now to the Figures, FIG. 1A illustrates a longitudinal cross-sectional view of a partially assembled subdermally implantable device 10 which contains central core 11 extending in an axial direction and having an outer surface 12 and opposing ends 13 and 13'. The central core contains a matrix of a pharmaceutically effective amount of subdermally administrable drug 14 substantially uniformly dispersed in a polymeric base material 15. An intermediate polymeric layer 16 overlies the outer surface 12 of the central core. Outer polymeric layer 17 having opposing ends 19 and 19' overlies intermediate layer 16. Ends 19 and 19' extend axially beyond opposing ends 13 and 13', respectively, of central core 11 to define cavities 20 and 20', respectively. Intermediate layer 16 controls the rate of diffusion of drug 14 from central core 11 to outer layer 17. Upon complete assembly of the device as shown in FIG. 1B, cavities 20 and 20' (not shown) are substantially filled with layers of a medical grade adhesive 18 and 18', respectively, to seal the opposing end portions 19 and 19', respectively, of outer layer 17, and to completely encapsulate the central core and the intermediate layer.

Base material 15 is any natural or synthetic polymeric material capable of forming a matrix with the drug, e.g., in which the drug is soluble, and which allows for the diffusion of the drug into the intermediate polymeric layer 16. Synthetic polymeric materials are preferred. Representative examples of same include aliphatic polyurethanes, e.g., Tecoflex®, polyurethane (Thermedics Corp., Woburn, Mass.), aromatic polyurethanes, silicone rubbers, e.g., polydimethylsiloxanes such as those sold under the trade name Silastic® (Dow Corning Co., Midland, Mich.), polyethylene-vinyl acetate copolymers, and polystyrene-butadiene copolymers. Silastic® polymers are more preferred. The polymeric base material can be solid, semi-solid or liquid, provided that it can be formed into the desired shape.

The subdermally administrable drug 14 is any physiologically or pharmacologically active substance which is capable of diffusing through the various layers of the instant devices and producing a localized or systemic therapeutic effect in mammals or animals when administered subdermally. Female contraceptive agents such as 3-keto-desogestrel, levonorgestrel, gestodene, and 16-methylene-17-α-acetoxy-19 nor-4-pregnene-3, 20-dione (also known as Nestorone™ progestin) are preferred. Among these agents, the Nestorone™ progestin is particularly preferred.

In general, however, the term "subdermally administrable drug" includes other entities such as anti-infectives, e.g., antibiotics; anti-allergenics; anti-inflammatories; decongestants; miotics and anti-cholinesterases; mydriatics; sympathomimetics; sedatives and hypnotics; tranquilizers and androgenic steroids; estrogens, e.g., estrone, 17 beta-estradiol, ethinyl estrodiol and diethyl stilbestrol; nutritional agents such as essential amino acids, fats, and vitamins; cardiovascular agents; anti-hypertensive agents; chemotherapeutic agents; progestational agents; and humoral agents; e.g., prostaglandins.

By the term "pharmaceutically effective," it is meant that amount which is sufficient to effect the desired change in the subject. The amount will vary depending upon such factors as the potency of the particular drug, the desired therapeutic effect, and the time span for which the implantable device is intended to provide treatment. Those skilled in the pharmaceutical arts will be able to determine both toxic levels and minimum effective doses of the drugs in accordance with standard procedures. For instance, a proper dosage form can be prepared by measuring the in vivo rate or elution of a given drug by standard analytic techniques, e.g., spectroscopic or radioimmunoassay analysis. In vitro diffusion of the drug from a delivery device of the present invention may be determined, for example, by the methods disclosed in Chien et al., J. Pharm. Sci., 63, 365 (1974), or by the methods described in U.S. Pat. No. 3,710,795.

In a preferred embodiment wherein the subdermally administrable drug is a female contraceptive agent, the "pharmaceutically effective" amount is that amount sufficient to result in contraception for a predetermined time period, e.g., the lifetime of the implant. The weight ratio of the polymeric base material to the contraceptive agent in the central core will generally range from about 0.67:1 to about 3:1. A preferred ratio is from about 1:1 to about 4.5:5.5. The implantable devices of the present invention contain a sufficient quantity of the agent which allows for a substantially constant release of the agent for about two years, at a daily dosage of from about 15 µg to about 80 µg. Thus, in general, the central core will contain from about 10 mg to about 85 mg of the contraceptive agent.

The intermediate polymeric layer 16 may be prepared from any natural or synthetic polymeric material. The polymeric material may be non-porous in which case the drug 14 is soluble, or porous in which case the drug is insoluble, and which provides for the diffusion of the drug through the pores of the layer into outer layer 17 at a rate less than the diffusion rate of the drug from the central core 11 to the intermediate layer. Examples of non-porous materials include ethylene/vinyl acetate copolymers having a vinyl acetate content of about 9% to about 12% by weight, polystyrene-butadiene copolymers, polyethylene terephthalate, and aliphatic urethanes. Porous materials are preferred. Suitable materials for forming the porous polymeric layer of the present invention include microporous polycarbonates comprised of linear polyesters of carbonic acid in which the carbonate groups recur in the polymer chain, by phosgenation of a dihydroxy aromatic such as bisphenol A; microporous poly (vinyl chlorides); microporous polyamides; microporous modacrylic copolymers; porous polysulfones; halogenated poly (vinylidene) fluoride; polychloroethers; acetal polymers; poly (urethanes); poly(amides); poly(benzimidazoles); cellulose esters; cellulose triacetate; cellulose; cellulose nitrate; regenerated cellulose; cross-linked poly (vinylpyrrolidone); anisotropic permeable microporous membranes of ionically associated polyelectrolytes; and the like. Preferred porous polymeric materials include cellulose, such as regenerated cellulose. More preferred are cellulose membranes having pore sizes from about 0.0025 to about 0.0050 microns, e.g., Spectra Por/2 and Spectra Por/4 membranes (Spectrum Medical Industries, Inc., Los Angeles, Calif.). While not intending to be bound by any particular theory. Applicants believe that the pores present in the preferred porous polymeric intermediate layer effectively reduce the overall surface area through which the drug can diffuse from the central core to the outer layer, and thus controls the diffusion rate of the drug from the device into the bodily tissue. In general, the thickness of the intermediate layer is from about 0.05 mm to about 0.10 mm.

Outer polymeric layer 17 which overlies the intermediate layer 16 is any natural or synthetic polymeric material compatible with bodily tissue and in which the drug 14 is permeable and which allows for the diffusion of the drug into the tissue of the subject. Suitable polymeric materials for forming the outer layer include polyethylene, polypropylene, ethylene/propylene copolymers, ethylene/ vinyl/acetate copolymers, silicone rubbers such as medical grade polydimethylsiloxanes, copolymers with vinyl acetates, poly-methacrylates, polymer (hydrogel), ethylene, propylene, polyethylene, ethylene vinyl/alcohol copolymers, ethylene/vinyl acetate/vinyl alcohol terpolymers, ethylene/vinyloxyethanol copolymers, hydrophilic polymers such as the hydrophilic hydrogels of esters of acrylic and methacrylic acids, modified collagen, cross-linked polyvinyl alcohol, and cross-linked, partially hydrolyzed polyvinyl acetate, and the like. In the embodiments of the present invention wherein the drug is a contraceptive agent such as a progestin, the outer layer is preferably made of a Silastic® polymer.

Adhesive layers 18 and 18' disposed in cavities 20 and 20', respectively, cooperate with overlying ends 19 and 19', respectively, of outer layer 17 to fully encapsulate the central core and the intermediate layer. The sealant minimizes the diffusion of the drug in the axial direction, i.e., from the ends of the device. It also serves to more securely hold the device together, e.g., maintain the structural integrity of the device, and prevents the infiltration of biological tissue into the otherwise open ends of the device. The central core and the intermediate layer can be sealed in a variety of ways in accordance with art-recognized techniques. For example, the overlying ends of the outer layer can be singed or pinched closed. The ends of the device may also be capped or plugged with a suitable biocompatible material. The potential for undesired axial diffusion of the drug increases as the length of the implant decreases, e.g., to about 3.0 cm and less. Thus, in these embodiments, it is preferred to first apply a layer of a plastic, e.g., polytetrafluoroethylene (PTFE) such as Teflon®, or other suitable material impermeable to the drug to the opposing ends of the central core and the intermediate layer.

The subdermally implantable devices of the present invention can be prepared in a variety of sizes and shapes to accommodate such factors as the specific implantation site and the desired release rate of the drug. In a preferred embodiment wherein the drug is a contraceptive agent, the device is substantially cylindrical in shape having a preferred overall length of from about 4.2 cm to about 4.6 cm, and a preferred overall diameter of from about 2.3 mm to about 2.7 mm. In such a case, the central core is rod-shaped, and has a preferred length of from about 3.8 cm to about 4.2 cm, and a preferred diameter of from about 2.0 mm to about 2.2 mm. These dimensions can be modified depending upon such factors as the implantation site and method of implantation, the subject, the condition to be treated, the drug, and the desired release rate of the drug, etc. For example, the length of the implantable device can be varied to deliver different amounts of the drug.

The subdermally implantable devices according to the present invention can be easily fabricated in accordance with standard techniques. Once the drug is mixed with the matrix material to achieve a substantially uniform dispersion, the desired shape of the resultant dispersion is achieved by molding, casting extrusion, or other appropriate process. When the matrix material contains polymers such as silicone elastomers, an additional curing step may be necessary. The intermediate layer is then applied to the thus-shaped matrix, e.g., by swelling, coating or laminating according to known techniques, a polymeric tube in water and then placing it over the matrix and allowing the polymer to dry in place, or by mechanical lapping. The outer layer can likewise be applied in a variety of ways such as by mechanical stretching, swelling or dipping. See, for example, U.S. Pat. Nos. 3,832,252, 3,854,480 and 4,957,119. The dimensions of the implant are also determined on the basis of the implantation method.

The devices of the present invention can be implanted into a subject in accordance with standard procedures. By the term "subject" it is meant mammals, e.g., humans, valuable domestic household, sport or farm animals, and laboratory animals. In the case of a contraceptive implant, for example, this procedure is advantageously performed with a trocar and the device is preferably implanted beneath the skin of the upper arm of the patient. See Shoupe et al., Am. J. Obstet. Gynecol. 160: 1286–92 (1989), and Tikkanen et al., J. Reprod. Med. 31: 898–905 (1986). Other implantation sites such as the buttocks and hip are also suitable. Although the devices of the present invention are preferably implanted subcutaneously, they may also be applied locally, e.g., in the cervical or uterine region, in which case the device is coupled to a string or some other means for retrieving it from the cervical canal or uterus, respectively. Thus, the term "subdermally" is meant to include all these aforementioned implantation sites.

The invention will be further described by reference to the following detailed examples. These examples are provided for purposes of illustration only, and are not intended to be limiting unless otherwise specified.

EXAMPLES

Example 1

Population

Volunteers were healthy women of proven fertility, 18 to 35 years old, regularly menstruating, not breast-feeding and with no contraindication for steroidal contraception. None had used injectable contraceptives or other steroidal contraceptives in the preceding year or had experienced a pelvic inflammatory disease since last pregnancy. All were regularly cohabitating and none used other contraceptives during the study. Women were informed of the purpose of the study and gave their consent.

Example 2
Preparation of the Nestorone™ Implants

The active ingredient, Nestorone™ progestin, 16-methylene-17-alpha-acetoxy-19 norprogesterone, and Silastic® elastomer (polymer base) were mixed together in a weight ratio of 1:1 such that each implant contained about 76–82 mg per implant, extruded and allowed to polymerize at room temperature, and then cut into the desired length. Using a mechanical device, a single layer of cellulose having approximately the same length, was wrapped around the thus extruded matrix. Silastic® tubing was swollen in the solvent n-hexane, and placed over the cellulose wrapped matrix. The solvent was evaporated, causing the Silastic® to form a layer around the cellulose. Both ends of the Silastic® tube were sealed with medical grade silicone Type A adhesive. The length of the drug containing rod was approximately 4 cm. The overall length of the implant (hereinafter "Implant A") was 4.4 cm with a diameter of 2.5 mm.

Implant B was prepared in the same manner as described above, except that Teflon barriers (2.2 mm in diameter and 0.127 mm in thickness) were placed at both ends of the core rod containing the Nestorone™ progestin.

Example 3
Admission and Follow-up

Seventy women were enrolled in the Nestorone™ implant group; twenty received Implant A and fifty received Implant B. Another 19 women using a Copper T IUD formed the control group. General physical, gynecological and breast examinations were done before admission and at each control visit. These were scheduled at the first and third months after admission and at three-month intervals thereafter. Women were encouraged to attend the clinic in case of complaints, menstrual irregularities or desire to stop treatment. PAP smears and hemoglobin (Hb) determination were done before admission and at yearly intervals. All women were given special cards for recording daily bleeding or spotting. A urinary pregnancy test was done routinely when menses were delayed by 15 days or more.

Implants were removed for medical reasons or at the request of the volunteers for any reason or at the end of the second year of use of the method.

Blood samples were obtained twice a week in the pretreatment cycle and for 5–6 consecutive weeks immediately after insertion and at weeks 24–30, 48–54, 72–77 and 96–104 for progesterone, estradiol and Nestorone™ progestin measurements in 40 implant users.

Example 4
Extraction and assay of Nestorone™ progestin from implants

Nestorone™ progestin in plasma was measured in Helsinki, Finland by radioimmunoassay, as described in (L ähteenmäki et al. Contraception 23: 63–75 (1981). To improve the sensitivity of the assay the extraction volume of plasma was increased to 0.5 mL. The assay sensitivity was 13.5 pmol/L and serum blank rarely exceeded this value. The intra- and interassay coefficient of variation in the optimal part of the standard curve were 9.3% and 16.1%, respectively. The interassay coefficients of variation for 400 pmol/L, 135 pmol/L and 27 pmol/L serum pools were 14.2%, 13.2% and 21.7%, respectively.

Recovered implants were each cut into small pieces (1–2 mm in thickness) and extracted for 24 h with absolute ethanol in a Soxhlet (Kontes® , Fischer Scientific) extraction apparatus. After cooling, the extract was quantitatively transferred to a 250 mL volumetric flask and made to mark with absolute ethanol. Appropriate dilutions of the extract were made in duplicate for analysis of Nestorone™ progestin. To test the efficiency of the extraction procedure, unused implants of known steroid contents served as controls and were subjected to the same extraction procedure as described above.

Standard solutions of Nestorone™ progestin were made in duplicate. Both standard and unknown solutions were read at 240 nm in a Perkin-Elmer Lambda 2 UV/VIS Absorption Spectrophotometer against a reference of absolute ethanol. Steroid recovery from control implants was (mean±S.D.) 99.1±2.3%.

Example 5
Data analysis

The clinical data of women using each type of implant were pooled for analysis since the results were similar. The occurrence of ovulation was indirectly assessed by plasma progesterone levels. When blood samples are obtained only twice weekly, progesterone values above 9.5 nmol/L were considered compatible with ovulation when accompanied in the preceding and/or following sample by values above 6.5 nmol/L. Those levels are achieved within 3–4 days after the LH peak in normal women where the occurrence of ovulation has been confirmed by the recovery of an oocyte from the fallopian tube. See Croxatto et al., Amer. J. Obstet. Gynecol. 132: 629–34 (1978). Levels above this threshold have never been observed in the follicular phase of the menstrual cycle in our control population. The endocrine pattern of each sampling period as assessed using the criteria described in Landgren et al., Contraception 21: 87–113 (1980), adapted to the 9.5 nmol/L of progesterone level used as threshold for corpus luteum function.

Descriptive statistics and ANOVA were used for comparison between groups. SAS Statistical Software (SAS Institute Inc., Box 8000, Cary, N.C.) was used for data analysis. Values of $p>0.05$ were considered significant.

Example 6
Results

The characteristics of the 70 acceptors of Nestorone™ implant were (X±S.D.) age: 27±5; weight: 56±1 Kg; parity 1 (46% or 2 (54%); and hemoglobin: 14±5 g/dL. Each acceptor's last pregnancy had ended 2 months to 12 years before admission.

No pregnancies occurred in 1570 woman-months observed. Ten women discontinued because of medical reasons: bleeding irregularities (n=4), hysterectomy for myoma (n=1,) ovarian teratoma (n=1,), headaches (n=2), one of which was associated with amenorrhea), low abdominal pain (n=1) and dizziness (n=1). Personal reasons for removal were planning pregnancy (n=4) and moving (n=1). One woman was lost to follow-up. The remaining 52 woman had implants removed at the end of the study.

The mean plasma levels of Nestorone™ observed during treatment (expressed in X±S.E.) declined from 112±8 pmol/L (Implant A) and 145±8 pmol/L (Implant B) during the first month of use to 86+3 pmol/L (Implant A) and 57+5 pmol/L (Implant B) at the end of the second year, respectively. The plasma levels of the progestin decreased during the two years of the study.

Plasma progesterone levels are shown in Table 1 according to the length of treatment.

TABLE I

Progesterone Plasma Levels in Women Treated with Nestorone™ Implants and in Control Women

| GROUP | Number of Sampling Periods* According to Highest Progesterone Level (nmol/L) | | | |
|---|---|---|---|---|
| | <9.5 | 9.5–16 | >16 | Samplings (n) |
| Implant | | | | |
| Week 1–6* | 37 | 2 | 1 | 40 |
| 24–29 | 37 | 1 | 0 | 38 |
| 48–53 | 34 | 0 | 0 | 34 |
| 72–77 | 34 | 0 | 2 | 36 |
| 98–103 | 24 | 2 | 4 | 30 |
| Total (n) | 166 | 5 | 7 | 178 |
| % | 93.3 | 2.8 | 3.9 | 100 |
| Control | | | | |
| Pretreatment | 0 | 0 | 40 | 40 |
| Copper T 380 A | 0 | 1 | 30 | 31 |
| Total (n) | 0 | 1 | 70 | 71 |
| % | 0 | 1.4 | 98.6 | 100 |

*Samples drawn twice a week for 5–6 consecutive weeks.
Differences between treated and control groups are highly significant ($p < 0.0001$).

Based on plasma progesterone levels below 9.5 nmol/L, it was estimated that ovulation was inhibited in 166 (93.3%) of 178 sampling periods in Nestorone™ implant users and in none of 71 control cycles ($p \leq 0.0001$). Isolated samples above 9.5 nmol/L occurred in 3 (1.7%) and 5 (7.0%) sampling periods in the treated and control group respectively, and were considered uncertain as to ovulation. Nine (5%) and 66 (93%) of the treated and control sampling periods were considered ovulatory, according to the criteria described. The proportion of sampling periods with plasma progesterone levels>16 nmol/L was significantly lower ($p<0.0001$) in treated than in control women (Table 1). The Nestorone™ progestin levels in women thought to be ovalatory cases ranged from 68 to 105 pmol/L. Out of the 178 sampling periods, 57 (32%) showed mean Nestorone™ progestin levels≧105 pmol/L.

The rate of steroid loss was greater for Implant A than for Implant B (data not shown). At 6, 12, 18 and 24 months of implant use, the estimated loss of Nestorone™ progestin was 21, 30, 39 and 49%, respectively, for Implant A and 12, 22, 32 and 42% respectively, for Implant B. Regardless of the implant design, approximately 50% of the original drug load remained in the implant after two years of use. At 6, 12, 18 and 24 months of use of Implant A, the average daily release rates of Nestorone™ progestin were 78, 69, 60 and 51 μg, respectively. By contrast, the rate approximates zero-order release for Implant B, resulting in a constant daily release of about 45 μg of Nestorone™ progestin for comparable time points.

These results indicate that women treated with Nestorone™ implants, 4 cm in length, having an estimated average daily in vivo release rate of approximately 50 μg/day, were effectively protected from pregnancy throughout the 2 years of use. The plasma levels of Nestorone™ progestin ranged from 112 pmol/L to 145 pmol/L in the early stage of treatment and from 86 pmol/L to 57 pmol/L at the end of the second year. Based on progesterone levels below 9.5 nmol/L, ovulation was inhibited in 166 (93.3%) out of 178 sampling periods. Nestorone™ progestin levels above 105 pmol/L were associated with a consistent inhibition of ovulation while 9 out of the 57 sampling periods below this threshold showed progesterone levels compatible with ovulation.

Figure 2A:
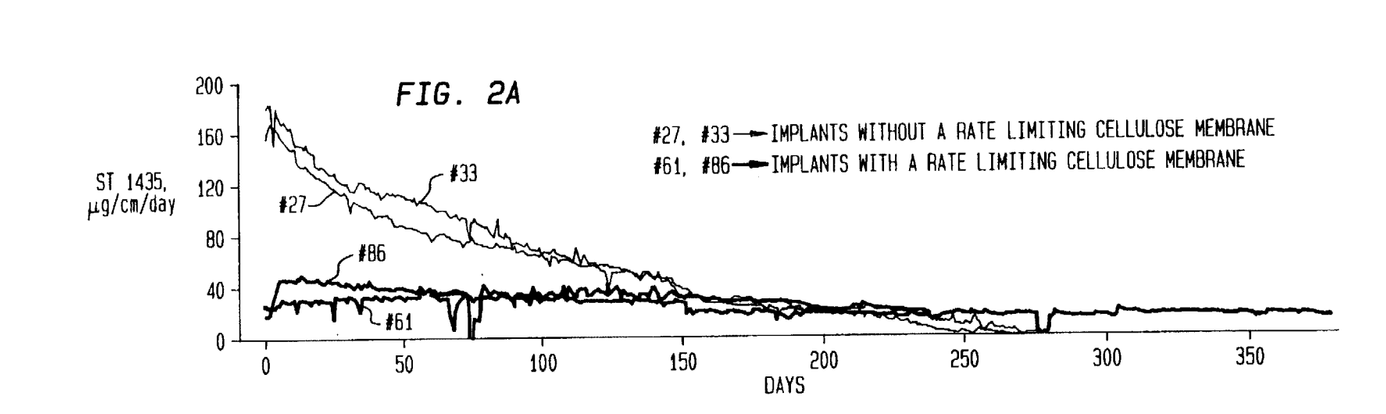
FIG. 2A is a graphical illustration of the in vitro release rates of Nestorone™ progestin from a device according to the present invention and from a prior art device.

Two additional experiments were conducted using the preferred contraceptive agents, the Nestorone™ progestin and 3-keto-desogestrel. The in vitro release rate of each of these agents was compared using implantable devices according to the present invention to devices which did not contain a rate limiting porous polymeric layer. More specifically, the implants of the present invention contained a Silastic®-contraceptive agent matrix, a layer of regenerated cellulose overlying the matrix and a Silastic® layer overlying the cellulose layer, and adhesive layers at the opposing ends. The prior art devices were identical to the instant devices, except for the absence of a cellulose layer. The results of the first experiment using the Nestorone™ progestin are graphically illustrated in FIG. 2A. These results clearly indicate that the prior art implants caused an initial overdose of the contraceptive agent, and were depleted as of about day 280. On the other hand, the implantable devices of the present invention achieved substantially zero-order release of the agent without any initial overdosing.

Figure 2B:
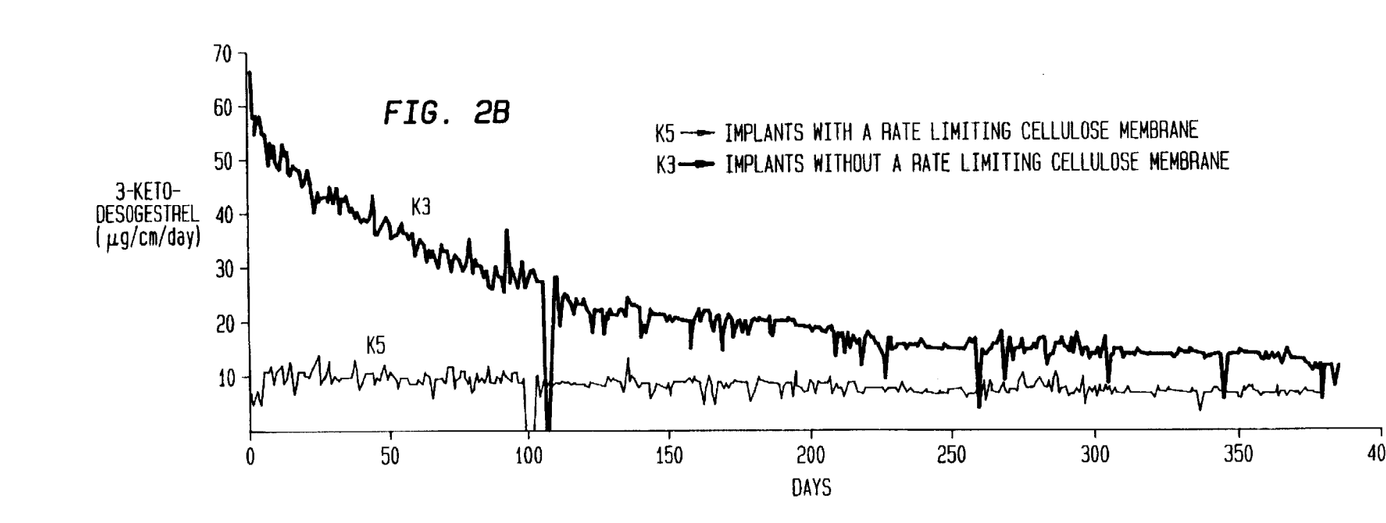
FIG. 2B is a graphical illustration of the in vitro release rates of 3-keto-desogestrel from a device according to the present invention and from a prior art device.

As illustrated in FIG. 2B, the implantable devices according to the present invention achieved substantially zero-order release of 3-keto-desogestrel, and without any initial overdosing of the contraceptive agent, whereas the prior art device caused significant overdosing.

The subdermally implantable devices of the present invention provide for a near, i.e., substantially, zero-order release of a pharmaceutically effective amount of a drug for a predetermined time period. Thus, reliable, long-term therapeutic benefits such as contraception may be obtained. The present invention offers the additional advantages of avoiding initial overdosing and the premature depletion of the drug. The present invention further obviates the need for a plurality of implants, and thus offers a simpler and more efficient means for delivering a therapeutic to a subject.

All publications and patent applications mentioned in this specification are indicative of the level of those skilled in the art to which this invention pertains. All these publications and patent applications are herein incorporated by reference to the same extent as if each individual publication or patent application were specifically and individually indicated to be incorporated by reference.

Various modifications of the invention described herein will become apparent to those skilled in the art. Such modifications are intended to fall within the scope of the appended claims.

We claim:

1. A method of contraception, comprising the step of subdermally administering an implantable contraceptive agent-delivery device to a subject, wherein said device comprises:
   a central core extending in an axial direction and having an outer surface and opposing ends, said core including a matrix of a contraceptive effective amount of a contraceptive agent substantially uniformly dispersed in a polymeric base material;
   an intermediate layer comprising a porous polymeric material overlying said outer surface of said central core; and
   an outer layer polymeric layer overlying said intermediate layer, wherein the said intermediate layer controls the rate of diffusion of said contraceptive agent from said central core to said outer layer.

2. A method according to claim 1, wherein said polymeric base material comprises an ethylene/vinyl acetate copolymer.

3. A method according to claim 1, wherein said polymeric base material comprises a silicone rubber.

4. A method according to claim 3, wherein said silicone rubber comprises a polydimethylsiloxane.

5. A method according to claim 1, wherein the contraceptive agent is 16-methylene-17-α-acetoxy-19-norprogesterone.

6. A method according to claim 1, wherein the contraceptive agent is 3-keto-desogestrel.

7. A method according to claim 1, wherein said polymeric base material and said contraceptive agent are present in said central core in a weight ratio of polymeric base material to contraceptive agent of from about 0.67:1 to about 3:1.

8. A method according to claim 7, wherein the ratio is from about 1:1 to about 4.5:5.5.

9. A method according to claim 1, wherein said porous polymeric material comprises a cellulosic material.

10. A method according to claim 1, wherein said porous polymeric material has pore sizes from about 0.0025 microns to about 0.0050 microns.

11. A method according to claim 1, wherein said outer polymeric layer comprises a silicone rubber.

12. A method according to claim 11, wherein said silicone rubber is a polysiloxane.

13. A method according to claim 1, wherein said device further comprises sealing means cooperating with said outer layer to fully encapsulate said central core and said intermediate layer.

14. A method according to claim 1, wherein said outer layer has opposing ends extending axially beyond said opposing ends of said central core to define cavities adjacent said opposing ends of said central core, and said sealing means comprises adhesive disposed in said cavities.

15. A method according to claim 14, wherein said sealing means further comprises a layer of polytetrafluoroethylene disposed between said opposing end of said central core and said adhesive in each of said cavities.

16. A method according to claim 1, wherein said device is substantially cylindrical in shape.

17. A method according to claim 1, wherein said device has an axial length of from about 4.2 cm to about 4.6 cm.

18. A method according to claim 1, wherein said device has a diameter of from about 2.5 mm to about 2.7 mm.

19. A method according to claim 1, wherein said central core has an axial length of from about 3.8 cm to about 4.2 cm.

20. A method according to claim 1, wherein said central core has a diameter of from about 2.0 mm to about 2.2 mm.

21. A method according to claim 1, wherein said intermediate layer has a thickness of from about 0.05 mm to about 0.10 mm.

22. A method according to claim 1, wherein said intermediate layer comprises cellulose.

23. A method according to claim 22, wherein said cellulose comprises regenerated cellulose.

24. The method of claim 1, wherein said device achieves substantially zero-order release of said contraceptive agent compared to contraceptive devices containing said central core and said outer layer but not said intermediate layer.

25. A method of contraception, comprising the step of subdermally administering an implantable device to a subject, wherein said device comprises:

a central core extending in an axial direction and having an outer surface and opposing ends, said core including a matrix of a pharmaceutically effective amount of a contraceptive agent substantially uniformly dispersed in a first polydimethylsiloxane elastomeric material;

an intermediate cellulosic layer overlying said outer surface of said central core; and an outer layer of a second polydimethylsiloxane elastomeric material overlying said intermediate cellulosic layer, wherein said intermediate cellulosic layer controls the rate of diffusion of said contraceptive agent from said central core to said outer layer.

26. A method according to claim 25, wherein said contraceptive agent comprises 16-methylene-17-α-acetoxy-19-norprogesterone.

27. A method according to claim 26, wherein said intermediate cellulosic layer comprises cellulose.

28. A method according to claim 27, wherein said cellulose comprises regenerated cellulose.

29. The method of claim 25, wherein said device achieves substantially zero-order release of said contraceptive agent compared to contraceptive devices containing said central core and said outer layer but not said intermediate cellulosic layer.

* * * * *

UNITED STATES PATENT AND TRADEMARK OFFICE
CERTIFICATE OF CORRECTION

PATENT NO. : 5,756,115
DATED : May 26, 1998
INVENTOR(S) : Moo-Young et al.

It is certified that error appears in the above-identified patent and that said Letters Patent is hereby corrected as shown below:

Face of Patent, Assignee, change "Coucil" to --Council--

Column 1, line 66, change "acetoxynorprogesterone-(Nestorone™)" to --acetoxy-norprogesterone-(Nestorone™)--

Column 8, line 62, change "57+5" to --57±5--

Signed and Sealed this

Twenty-fifth Day of August, 1998

Attest:

BRUCE LEHMAN

*Attesting Officer*          *Commissioner of Patents and Trademarks*